United States Patent [19]
Duckworth et al.

[11] Patent Number: 5,905,080
[45] Date of Patent: May 18, 1999

[54] AMIDE AND UREA DERIVATIVES AS 5HT1D RECEPTOR ANTAGONISTS

[75] Inventors: David Malcolm Duckworth; Laramie Mary Gaster, both of Bishop's Stortford; Sarah Maragaret Jenkins, Harlow; Andrew John Jennings, Bengeo; Keith Raymond Mulholland, Harlow, all of United Kingdom

[73] Assignee: SmithKline Beecham, p.l.c., Brentford, United Kingdom

[21] Appl. No.: 08/596,223

[22] PCT Filed: Aug. 9, 1994

[86] PCT No.: PCT/EP94/02662

§ 371 Date: Feb. 15, 1996

§ 102(e) Date: Feb. 15, 1996

[87] PCT Pub. No.: WO95/06044

PCT Pub. Date: Mar. 2, 1995

[30]  Foreign Application Priority Data

| | | | |
|---|---|---|---|
| Aug. 20, 1993 | [GB] | United Kingdom | 9317328 |
| Aug. 20, 1993 | [GB] | United Kingdom | 9317333 |
| Sep. 2, 1993 | [GB] | United Kingdom | 9318186 |
| Nov. 3, 1993 | [GB] | United Kingdom | 9322630 |

[51] Int. Cl.$^6$ ............... A61K 31/495; C07D 401/12; C07D 409/12; C07D 295/135

[52] U.S. Cl. ............... 514/252; 514/255; 544/360; 544/364; 544/379; 544/393

[58] Field of Search ............... 544/393, 360, 544/379, 364; 514/252, 255

[56]  References Cited

U.S. PATENT DOCUMENTS

| | | | |
|---|---|---|---|
| 4,735,959 | 4/1988 | Grell et al. | 514/357 |
| 5,055,469 | 10/1991 | Mitsumuri et al. | 514/252 |
| 5,696,122 | 12/1997 | Gaster et al. | 514/251 |
| 5,807,860 | 9/1998 | Inoue et al. | 514/255 |

FOREIGN PATENT DOCUMENTS

| | | |
|---|---|---|
| 0 058 779 A2 | 9/1982 | European Pat. Off. . |
| 0 533 266 A1 | 3/1993 | European Pat. Off. . |
| 0 533 267 A1 | 3/1993 | European Pat. Off. . |
| 0 533 268 A1 | 3/1993 | European Pat. Off. . |
| 2.163.519 | 7/1973 | France . |

OTHER PUBLICATIONS

Lamothe et al, Synlett., pp. 507–508 Jun. 1986.
Saxena, *Pharmac. Ther.* 66, pp. 339–368 1995.
James J. Krutak, et a., *Third Journal of Organic Chemistry*, 44(22), pp. 3847–3858 (Oct. 26, 1979).

*Primary Examiner*—Emily Bernhardt
*Attorney, Agent, or Firm*—Wayne J. Dustman; Charles M. Kinzig; Stephen A. Venetianer

[57] ABSTRACT

Novel amide and urea derivatives, processes for their preparation, pharmaceutical compositions containing hem and their use as medicaments are disclosed.

8 Claims, No Drawings

AMIDE AND UREA DERIVATIVES AS 5HT1D RECEPTOR ANTAGONISTS

The present invention relates to novel amide and urea derivatives, processes for their preparation, and pharmaceutical compositions containing them.

EPA 0 533 266/7/8 disclose a series of benzanilide derivatives which are said to possess $5HT_{1D}$ receptor antagonist activity. These compounds are alleged to be of use in the treatment of various CNS disorders.

A structurally distinct class of compounds have now been discovered and have been found to exhibit $5HT_{1D}$ antagonist activity. In a first aspect, the present invention therefore provides a compound of formula (I) or a salt thereof:

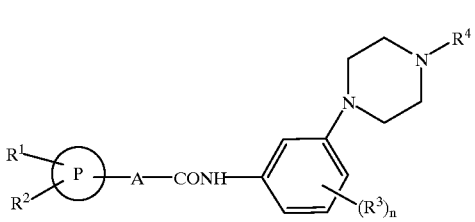

in which

P is phenyl or a 5 to 7-membered heterocyclic ring containing 1 to 3 heteroatoms selected from oxygen, nitrogen or sulphur, $R^1$ is hydrogen, halogen, $C_{1-6}$alkyl, $C_{3-6}$cycloalkyl, $C_{3-6}$cycloalkenyl, $C_{1-6}$alkoxy, hydroxy, hydroxy$C_{1-6}$alkyl, acyl, nitro, trifluoromethyl, cyano, $SR^5$, $SOR^5$, $SO_2R^5$, $SO_2NR^5R^6$, $CO_2R^5$, $CONR^5R^6$, $CONR^5(CH_2)CO_2R^6$, $NR^5R^6$, $NR^5CO_2R^6$, $CR^5=NOR^6$, where $R^5$ and $R^6$ are independently hydrogen or $C_{1-6}$alkyl and p is 1 to 3;

or $R^1$ is optionally substituted phenyl or an optionally substituted 5 to 7-membered heterocyclic ring containing 1 to 3 heteroatoms selected from oxygen, nitrogen or sulphur, $R^2$ is is hydrogen, halogen, $C_{1-6}$alkyl, $C_{3-6}$cycloalkyl, $C_{3-6}$cycloalkenyl, $C_{1-6}$alkoxy, hydroxy, hydroxy$C_{1-6}$alkyl, acyl, nitro, trifluoromethyl, cyano, $SR^5$, $SOR^5$, $SO_2R^5$, $SO_2NR^5R^6$, $CO_2R^5$, $CONR^5R^6$, $CONR^5(CH_2)_p CO_2R^6$, $NR^5R^6$, $NR^5CO_2R^6$, $CR^5=NOR^6$, where $R^5$, $R^6$, and p are as defined for $R^1$;

$R^3$ is hydrogen, halogen, hydroxy, $C_{1-6}$alkyl or $C_{1-6}$alkoxy;

$R^4$ is hydrogen or $C_{1-6}$alkyl;

A is NH or an acyclic hydrocarbon chain having 1 to 6 carbon atoms; and n is 1 or 2.

The groups P and $R^1$ can be aromatic or saturated heterocyclic rings. Examples of suitable aromatic heterocyclic rings include thienyl, furyl, pyrrolyl, triazolyl, diazolyl, isothiazolyl, isoxazolyl, oxadiazolyl, thiadiazolyl, pyridyl, pyrimidyl and pyrazinyl. When P or $R^1$ is a saturated ring examples include piperidine, morpholine and piperazine rings. The groups P and $R^1$ can be linked to the remainder of the molecule via a carbon atom or, when present, a nitrogen atom.

Optional substituents for $R^1$ phenyl and heterocyclic rings include halogen, $C_{1-6}$alkyl, $C_{3-6}$cycloalkyl, $C_{3-6}$cycloalkenyl, $C_{1-6}$alkoxy, hydroxy, acyloxy, cyano, nitro, amino, $CO_2R^5$ where $R^5$ is hydrogen or $C_{1-6}$alkyl, or $CONR^6R^7$ where $R^6$ and $R^7$ are hydrogen or $C_{1-6}$alkyl.

Preferably P is phenyl or thienyl.

Preferably $R^1$ is hydrogen, halogen, phenyl, or pyridyl.

Preferably $R^2$ is hydrogen or $C_{1-6}$alkyl, for example methyl.

Preferably $R^3$ is $C_{1-6}$alkoxy such as methoxy.

The integer n can be 1 or 2. Preferably n is 1.

Preferably $R^4$ is $C_{1-6}$alkyl such as methyl.

Suitably A is NH or an acyclic hydrocarbon chain having 1 to 6 carbon atoms. For the avoidance of doubt, the term 'chain of 1 to 6 carbon atoms' means carbon atoms extending in a branched or unbranched chain between the group P and the amide group. The hydrocarbon chain A can be an alkylene chain, for example methylene or ethylene, or A can contain alkene or alkyne groups. Preferably A is NH or an $C_{2-4}$alkene group, in particular a CH=CH group.

$C_{1-6}$alkyl groups, whether alone or as part of another group, may be straight chain or branched.

Particularly preferred compounds of the invention include:

N-[4-methoxy-3-(4-methyl-1-piperazinyl)phenyl]-4-bromophenylacetamide,

N-(4 methoxy-3-(4-methyl-1-piperazinyl)phenyl)-4-bromocinnamide,

N-[4-methoxy-3-(4-methyl-1-piperazinyl)phenyl]-3-(thien-3-yl)acrylamide,

N-(4-methoxy-3-(4-methyl-1-piperazinyl)phenyl)-4-(4-pyridyl)cinnamide,

N-(4-methoxy-3-(4 methyl-1-piperazinyl)phenyl)-4-phenylcinnamide,

N-(4-methoxy-3-(4-methyl-1-piperazinyl)phenyl)-5-phenylpenta-2,4-dienamide,

N-(4-bromophenyl)-N'-[4-methoxy-3-(4-methyl-1-piperazinyl)phenyl]urea,

N-(4-bromo-3-methylphenyl)-N'-[4-methoxy-3-(4-methyl-1-piperazinyl)phenyl]urea,

N-[3-methyl-4-(4-pyndyl)phenyl]-N'-[4-methoxy-3-(4-methyl-1 piperazinyl)phenyl]urea, or N-(4-methoxy-3-(1-piperazinyl)phenyl)-4-(4-pyridyl)cinnamide, and pharmaceutically acceptable salts thereof.

Preferred salts of the compounds of formula (I) are pharmaceutically acceptable salts. These include acid addition salts such as hydrochlorides, hydrobromides, phosphates, acetates, fumarates, maleates, tartrates, citrates, oxalates, methanesulphonates and p-toluenesulphonates.

Certain compounds of formula (I) are capable of existing in stereoisomeric forms. It will be understood that the invention encompasses all geometric and optical isomers of the compounds of formula (I) and the mixtures thereof including racemates. Tautomeric forms of compounds of formula (I) and mixtures thereof are also included within the scope of the invention.

In a further aspect the present invention provides a process for the preparation of a compound of formula (1) which comprises:

(a) for compounds in which A is an acyclic hydrocarbon chain reaction of a compound of formula (II):

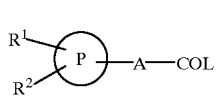

in which A is an acyclic hydrocarbon chain and $R^1$, $R^2$ and P are as defined in formula (I) and L is a leaving group, with a compound of formula (III):

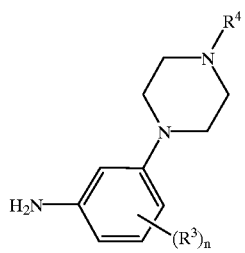

in which $R^3$, $R^4$ and n are as defined in formula (I); or
(b) reaction of a compound of formula (IV):

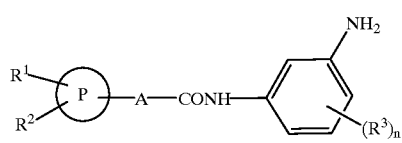

in which $R^1$, $R^2$, $R^3$, P, A and n are as defined in formula (I) with a compound of formula (V):

in which $R^4$ is as defined in formula (I) and Hal is halogen, or
(c) for compounds where $R^1$ is a phenyl or heterocyclic ring, reaction of a compound of formula (VI):

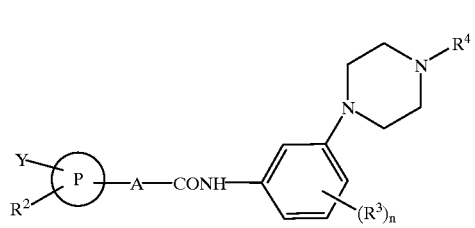

in which $R^2$, $R^3$, $R^4$, P, A and n are as defined in formula (I) and Y is halogen or a group $-OSO_2CF_3$ with a compound of formula (VII):

in which $R^1$ is a phenyl or heterocyclic ring as defined in formula (I), or
(d) for compounds where $R^1$ is a phenyl or heterocyclic ring, reaction of a compound of formula (VIII):

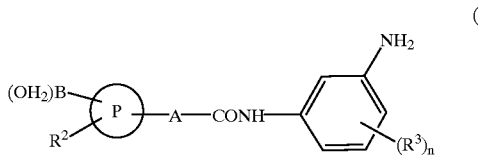

in which $R^2$, $R^3$, $R^4$, P, A and n are as defined in formula (I) with a compound of formula (IX):

in which $R^1$ is as defined in formula (VII) and Y is as defined in formula (VI), or (e) when A is a NH group:
coupling a compound of formula (X):

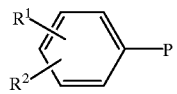

with a compound of formula (XI):

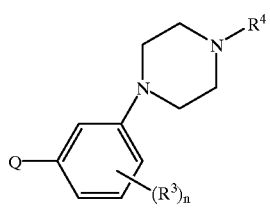

wherein $R^1$, $R^2$, $R^3$, $R^4$ and n are as defined in formula (I) and P and Q are functional groups which when coupled form the $-NHCONH-$ linkage;
and optionally after any of the above processes:
  converting a compound of formula (I) into another compound of formula (I).
  forming a pharmaceutically acceptable salt.

Suitable activated carboxylic acid derivatives of formula (II) include acyl halides and acid anhydrides. Activated compounds of formula (II) can also be prepared by reaction of the corresponding carboxylic acid with a coupling reagent such as carbonyldiimidazole, dicyclohexylcarbodiimide or diphenylphosphorylazole. Preferably the group L is halo, particularly chloro.

A compound of formula (II) is typically reacted with a compound of formula (I) in an inert organic solvent such as DMF, THF or dichloromethane at ambient or elevated temperature in the presence of a base such as triethylamine or pyridine.

Compounds of formula (II) can be prepared from a compound of formula (XII):

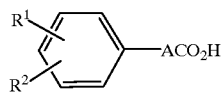

in which $R^1$, $R^2$, and A are as defined in formula (II) using standard procedures. For example acid chlorides can be prepared by reaction with phosphorous pentachloride, oxalyl chloride or thionyl chloride. Acid anhydrides can be prepared by reaction with a suitable acid anhydride, for example trifluoroacetic anhydride.

Reaction of a compound of formula (IV) with a compound of formula (V) is suitably carried out in an alcohol or nitrile solvent with an optional base or, alternatively, in a non-polar solvent such as chlorobenzene in the absence of base. Suitably, the reactions are carried out at ambient or elevated temperature, preferably at the reflux temperature of the reaction mixture.

Reaction of compounds of formula (VI) and (VII) and reaction of compounds of formulae (VIII) and (IX) can be carried out in the presence of a transition metal catalyst such as $Pd(PPh_3)_4$ in a solvent such as an ether in the presence of a base such as an alkali metal carbonate or bicarbonate, for example sodium carbonate or bicarbonate, at ambient or elevated temperature.

It will be apparent to those skilled in the art that compounds in which the A linkage contains a double bond can be prepared using standard Wittig chemistry.

In the reaction of a compound of formula (X) with a compound of formula (XI) suitable examples of groups P and Q include:
- (i) P is —N=C=O and Q is —NH$_2$,
- (ii) P is —NHCOL and Q is —NH$_2$,
- (iii) P is —NH$_2$ and Q is NHCOL,
- (IV) P is NH$_2$ and Q is —N=C=O, where L is a leaving group. Examples of suitable leaving groups L include halogen such as chloro, bromo, imidazole or phenoxy or phenylthio optionally substituted for example with halogen.

When P is —N=C=O and Q is NH$_2$ or when P is NH$_2$ and Q is —N=C=O the reaction is suitably carried out in an inert solvent for example dichloromethane or toluene at ambient temperature.

When P is —NHCOL and Q is —NH$_2$ or when P is —NH$_2$ and Q is —NH$_2$COL, the reaction is suitably carried out in an inert solvent such as dichloromethane at ambient temperature optionally in the presence of a base, such as triethylamine or in dimethylformamide at ambient or elevated temperature.

Compounds of formulae (XI) or (XII) in which P or Q respectively is —N=C=O may be prepared by treating a compound of formula (II) in which:
- i) P or Q is amino, with phosgene or a phosgene equivalent, in the presence of excess base in an inert solvent.
- ii) P or Q is acylazide (i.e. CON$_3$), via the nitrene, by thermal rearrangement using conventional conditions (ref L.S. Trifonov et al, Helv. Chim. Acta 1987 70 262).
- iii) P or Q is CONH$_2$, via the nitrene intermediate using conventional conditions.

Compounds of formulae (X) or (XI) in which P or Q respectively is NH$_2$COL may be prepared by reacting a compound of formulae (X) or (XI) in which P or Q is NH$_2$ with phosgene or a phosgene equivalent in an inert solvent, at low temperature, if necessary in the presence of one equivalent of a base such as triethylamine.

Examples of phosgene equivalents include triphosgene, carbonyldiimidazole, phenyl chloroformate and phenyl chorothioformate.

Intermediate compounds of formulae (III), (IV), (V), (VI), (VII), (VIII), (IX), (X) and (XII) are commercially available or can be prepared using standard procedures such as those outlined in EPA 53326617/8.

It will be appreciated to those skilled in the art that it may be necessary to protect certain reactive substituents during some of the above procedures, for example when the group R$^4$ is a hydrogen atom. Standard protection and deprotection techniques can be used. For example, primary amines can be protected as phthalimide, benzyl, benzyloxycarbonyl or trityl derivatives. These groups can be removed by conventional procedures.

Carboxylic acid groups can be protected as esters. Aldehyde or ketone groups can be protected as acetals, ketals, thioacetals or thioketals. Deprotection is achieved using standard conditions.

Compounds of formula (I) can be converted into further compounds of formula (I) using standard techniques. For example, in the case wherein R$^4$ is hydrogen, it is possible to introduce a C$_{1-6}$alkyl group by conventional alkylation using 1 molar equivalent of a C$_{1-6}$alkyl halide and 1 molar equivalent of a suitable base in an inert solvent. Compounds of formula (I) in which R$^1$ or R$^2$ contain carboxylic acid groups can be esterified using normal procedures.

5HT$_{1D}$ Antagonists, and in particular the compounds of the present invention, are expected to be of use in the treatment of CNS disorders such as mood disorders, including depression, seasonal effective disorder and dysthymia; anxiety disorders, including generalised anxiety, panic disorder, agoraphobia, social phobia, obsessive compulsive disorder and post-traumatic stress disorder, memory disorders, including dementia, amnestic disorders and age-associated memory impairment; and disorders of eating behaviours, including anorexia nervosa and bulimia nervosa. Other CNS disorders include Parkinson's disease, dementia in Parkinson's disease, neuroleptic-induced Parkinsonism and tardive dyskinesias, as well as other psychiatric disorders.

5HT$_{1D}$ Antagonists, and in particular compounds of the present invention, may also be of use in the treatment of endocrine disorders such as hyperprolactinaemia, in the treatment of vasospasm (particularly in the cerebral vasculature) and hypertension, as well as disorders in the gastrointestinal tract where changes in motility and secretion are involved. They may also be of use in the treatment of sexual dysfunction.

Therefore, the present invention, provides a compound of general formula (I) or a physiologically acceptable salt or solvate thereof for use in therapy.

The present invention also provides a compound of general formula (I) or a physiologically acceptable salt or solvate thereof for use in the treatment of the aforementioned disorders.

In another aspect the invention provides the use of a compound of general formula (I) or a pharmaceutically acceptable salt or solvate thereof for the manufacture of a medicament for the treatment of the aforementioned disorders.

In a further aspect the invention provides a method of treating the aforementioned disorders which comprises administering an effective amount to a patient in need of such treatment of a compound of general formula (I) or a pharmaceutically acceptable salt or solvate thereof.

In particular the invention provides a compound of general formula (I) or a physiologically acceptable salt or solvate thereof for use in the treatment or prophylaxis of depression.

It will be appreciated by those skilled in the art that the compounds according to the invention may advantageously be used in conjunction with one or more other therapeutic agents, for instance, different antidepressant agents.

The present invention also provides a pharmaceutical composition, which comprises a compound of formula (I) or a pharmaceutically acceptable salt thereof, and a pharmaceutically acceptable carrier.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colorants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterlisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 200 mg, and such unit doses may be administered more than once a day, for example two or three a day. Such therapy may extend for a number of weeks or months. When administered in accordance with the invention, no unacceptable toxicological effects are expected with the compounds of the invention.

The following Examples illustrate the preparation of compounds of the invention.

EXAMPLE 1

N-[4-Methoxy-3-(4-methyl-1-piperazinyl)phenyl]-4-bromophenylacetamide

4Bromophenylacetic acid (0.300 g, 1.40 mmol) was suspended in thionyl chloride (10 ml) and heated to reflux with stirring. After 1 h, the reaction mixture was allowed to cool and was evaporated under reduced pressure to give a yellow oil. The oil was then azeotroped with toluene, and the residue dried in vacuo to give the crude acid chloride. Meanwhile 4-methoxy-3-(4-methyl-1-piperazinyl) benzeneamine (EP 0533 267 A1) (0.293 g, 1.33 mmol) was dissolved in dichloromethane (10 ml) and treated with triethylamine (0.195 ml, 1.40 mmol), followed by dropwise addition of a solution of the crude acid chloride in dichloromethane (3 ml). The mixture was stirred at room temperature overnight before being washed with $NaHCO_3$ solution. The organic layer was then dried ($Na_2SO_4$), and was evaporated under reduced pressure to give a brown oil. The oil was purified by silica-gel chromatography (5% $MeOH/CH_2Cl_2$ as eluant) to give the title compound as a pale yellow oil (0.295 g, 50%), which was converted to its oxalate salt.

m.pt 118–120° C.; $^1$H NMR (250 MHz, $CDCl_3$) free base δ 7.52 (d, 2H), 7.30–7.13 (m, 3H), 7.05 (m, 2H), 6.78 (d, 1H), 3.82 (s,3H), 3.65 (s, 2H), 3.08 (br s, 4H), 2.63 (br s, 4H), 2.36 (s, 3H).

EXAMPLE 2

N-(4-Methoxy-3-(4-methyl-1-piperazinyl)phenyl)-4-bromocinnamide

4-Bromocinnamic acid (350 mg, 1.54 mmol) was heated at reflux with thionyl chloride (3 ml) and toluene (40 ml) for 2 h, and then evaporated to dryness under reduced pressure. 4-Methoxy-3-(4-methyl-1-piperazinyl)phenylamine (320 mg, 1.54 mmol) in dry dichloromethane (40 ml) was added with triethylamine (1 ml) and the mixture stirred for 1 h. The solution was partitioned between dichloromethane (40 ml) and saturated aqueous potassium carbonate (40 ml), the organic solution dried (sodium sulphate) and evaporated to dryness under reduced pressure to afford an oil, which was purified by column chromatography (silica, chloroform/methanol 5%) to afford the title compound (570 mg, 92%) which was crystallised from methanol/diethyl ether as the oxalate salt.

1H nmr (d6-DMSO) δ 2.90 (3H, s), 3.38 (8H, bs), 3.89 (3H, s), 6.92 (1H, d), 7.06 (1H, d), 7.48 (2H, m), 7.65 (3H, m), 7.74 (2H, d), 10.28 (1H, s, NH). Elemental analysis C 51.79, H 4.92, N 7.87% $C_{21}H_{24}N_3O_2Br.C_2H_2O_4.H_2O$ requires C 51.30, H 5.20, N 7.81%

EXAMPLE 3

N-[4-methoxy-3-(4-methyl-1-piperazinyl)phenyl]-3-(thien-3-yl)acrylamide

3-Thien-3-yl)acrylic acid (0.50 g;3.25 mmol) was heated at reflux in thionyl chloride (10 ml) for 1 hour, evaporated in vacuo and residue redissolved in dry $CH_2Cl_2$ (10 ml). The acid chloride was treated with 4-methoxy-3-(4-methyl-1-piperazinyl)benzenamine (0.718 g;3.25 mmol) and triethylamine (0.45 ml;3.25 mmol) then stirred at RT for 18 hours. The solution was evaporated in vacuo, the residue partitioned $H_2O$ $CHCl_3$, the organics dried over $Na_2SO_4$, filtered and the filtrate evaporated in vacuo to an dark orange residue. The residue was purified by flash silica-gel chromatography and eluted with 2%$MeOH/CHCl_3$ to yield the title compound as a lemon solid (0.28 g;24%) after trituration with petrol.

$^1$H NMR (250 MHz, $CDCl_3$) δ: 7.80–7.60(m,2H), 7.45 (d,1H), 7.35–7.25(m,4H), 6.80(d,1H), 6.40(d,1H), 3.85(s, 3H), 3.20–3.00(s,4H), 2.70–2.50(s,4H), 2.35(s,3H)

EXAMPLE 4

N-(4-Methoxy-3-(4-methyl-1-piperazinyl)phenyl)-4-(4-pyridyl)cinnamide

N-(4-Methoxy-3-(4-methyl-1-piperazinyl)phenyl)-4-bromocinnamide (350 mg, 0.81 mmol), sodium carbonate (95 mg, 0.81 mmol), tetrakis-(triphenylphosphine)palladium (0) (50 mg, 0.05 equiv), 4-pyridylboronic acid (110 mg, 0.81 mmol) in water (18 ml) and DME (18 ml) were heated at reflux under argon for 18 h. The solution was partitioned between chloroform (40 ml) and saturated aqueous potassium carbonate (40 ml), the organic solution dried (sodium sulphate) and evaporated to dryness under reduced pressure to afford an oil, which was purified by flash column chromatography (silica, chloroform/methanol 5%) to afford the title compound (223 mg, 71%) which was crystallised from methanol/diethyl ether as the oxalate salt m.p. 224–226° C.

1H nmr (d6DMSO) d 2.83 (3H, s, NMe), 3.35 (8H, m), 3.82 (3H, s, OMe), 6.94 (2H, m), 7.40 (2H, s), 7.62 (1H, d), 7.78 (4H, m), 7.90 (2H, d), 8.69 (2H, d), 10.2 3(1H, s, NH). Mass spectrum M$^+$ 428 C$_{23}$H$_{28}$N$_4$O$_2$ requires 428. Elemental analysis C 58.35, H 5.23, N 9.08% C$_{23}$H$_{28}$N$_4$O$_2$.2.2 (C$_2$H$_2$O$_4$) requires C 58.27, H 5.18, N 8.95%

EXAMPLE 5

N-(4-Methoxy-3-(4-methyl-1-piperazinyl)phenyl)4-phenylcinnamide

N-(4-Methoxy-3-(4-methyl-1-piperazinyl)phenyl) 4bromocinnamide(350 mg, 0.81 mmol), sodium carbonate (95 mg, 0.81 mmol), tetrakis (triphenylphosphine)palladium (0) (50 mg, 0.05 equiv), benzeneboronic acid (110 mg, 0.81 mmol) in water (18 ml) and DIME (18 ml) were heated at reflux under argon for 18 h. The solution was partitioned between chloroform (40 ml) and saturated aqueous potassium carbonate (40 ml), the organic solution dried (sodium sulphate) and evaporated to dryness under reduced pressure to afford an oil, which was purified by flash column chromatography (silica, chloroform/methanol 5%) to afford the title compound (278 mg, 88%) which was crystallised from methanol/diethyl ether as the oxalate salt. m.p. 110–115 and 177–179° C.

1H nmr (d6-DMSO) d 2.80 (3H, s, NMe), 3.29 (8H, m), 3.80 (3H, s, OMe), 6.87 (1H, d), 6.96 (1H, d), 7.40 (3H, m), 7.50 (2H, t), 7.61 (1H, d),7.75 (5H, m), 10.20 (1H, s, NH). Mass spectrum M$^+$ 427 C$_{27}$H$_{22}$N$_3$O$_2$ requires 427. Elemental analysis C 64.87, H 6.02, N 7.80% C$_{27}$H$_{22}$N$_3$O$_2$.1.4 (C$_2$H$_2$O$_4$) requires C 64.67, H 5.75, N 7.59%

EXAMPLE 6

N-(4-Methoxy-3-(4-methyl-1-piperazinyl)phenyl)-5-phenylpenta-2,4-dienamide

5-Phenylpenta-2,4-dienoic acid (270 mg, 1.55 mmol) was heated at reflux with thionyl chloride (3 ml) and toluene (40 ml) for 2 h, and then evaporated to dryness under reduced pressure. 4-Methoxy-3-(4-methyl-1-piperazinyl) phenylamine (340 mg, 1.55 mmol) in dry dichloromethane (40 ml) was added with triethylamine (1 ml) and the mixture stirred for 1 h. The solution was partitioned between dichloromethane (40 ml) and saturated aqueous potassium carbonate (40 ml), the organic solution dried (sodium sulphate) and evaporated to dryness under reduced pressure to afford an oil, which was purified by column chromatography (silica, chloroform/methanol 5%) to afford the title compound (595 mg, 100%) which was crystallised from methanol/diethyl ether as the oxalate salt.

1H nmr (d6-DMSO) δ 2.78 (3H, s), 3.24 (8H, bs), 3.79 (3H, s), 6.32 (1H, d), 7.06(3H, m), 7.35 (6H, m), 7.62 (2H, d), 10.05 (1H, s, NH). Mass Spectrum M$^+$ found 377 C$_{23}$H$_{27}$N$_3$O$_2$ requires 377 Elemental analysis C 62.17, H 6.05, N 8.69% C$_{23}$H$_{27}$N$_3$O$_2$.1.3C$_2$H$_2$O$_4$ requires C 62.18, H 6.03, N 8.50%

EXAMPLE 7

N-(4-Bromophenyl)-N'-[4-methoxy-3-(4-methyl-1-piperazinyl)phenyl]urea

A mixture of 4-bromophenyl isocyanate (0.179 g, 0.905 mmol) and 4-methoxy-3-(4-methyl-1-piperazinyl) benzeneamine (EP 0 533 267 A1) (0.200 g, 0.905 mmol) in toluene were stirred together at room temperature. After 24 h, the resultant precipitate was filtered off, washed with petrol and dried in vacuo to give the title compound as a white solid (0.265 g, 70%). m.pt 199–201° C.

1H NMR (250 MHz, CD$_3$SOCD$_3$), δ 8.69 (s, 1H), 8.48 (s, 1H), 7.43 (s, 4H), 7.02 (d, 1H), 6.94 (dd, 1H), 6.83 (d, 1H), 3.73 (s, 3H), 2.95 (s, 4H), 2.30 (s, 4H), 2.21 (s,3H).

EXAMPLE 8

N-(4-bromo-3-methylphenyl)-N'-[4-methoxy-3-(4-methyl-1-piperazinyl)phenyl]urea 4Methoxy-3-(4-methyl-1-piperazinyl)benzeneamine (EP 0 533 267 A1) was added to a stirred solution of 1,1-carbonyldiimidazole (0.242 g, 1.49 mmol) in dichloromethane (20 ml). After 0.5 h, the reaction mixture was evaporated under reduced pressure and redissolved in dimethylformamide (10 ml). The resultant mixture was then treated with 4-bromo-3-methylaniline (0.253 g, 1.36 mmol), and stirred at room temperature overnight. Water (35 ml) was then added and the resultant precipitate was filtered off and dried in vacuo to give the title compound as a pale brown solid (0.400 g, 68%).

m.pt 190–191° C. $^1$H NMR (200 MHz, CD$_3$SOCD$_3$), δ 8.76 (s,1H), 8.62 (s, 1H), 7.54 (m, 2H), 7.35 (dd, 1H), 7.17 (m, 2H), 6.99 (d, 1H), 3.88 (s, 3H), 3.09 (br s, 4H), 2.60 (br s, 4 H),2,44 (s, 3H), 2.35 (s, 3H).

EXAMPLE 9

N-[3-Methyl4-(4-pyridyl)phenyl]-N'-[4-methoxy-3-(4-methyl-1-piperazinyl)phenyl]urea The product from example 2 (0.300 g, 0.693 mmol), and 4-pyridylboronic acid (0.085 g, 0.693 mmol) were dissolved in 1,2-dimethoxyethane (16 ml), and sodium carbonate (0.220 g, 2.08 mmol) in water (4 ml) was added, followed by tetrakis(triphenylphosphine)palladium(0) (20 mg) under argon. The mixture was then heated under reflux. After 18 h, further amounts of palladium catalyst (20 mg) and 4-pyridylboronic acid (0.021 g, 0.173 mmol) were added. Reflux was then maintained for a further 2 h. The reaction mixture was then allowed to cool and was partitioned between dichloromethane and water. The aqueous layer was then extracted with dichloromethane (1×), and the combined organic layers were dried (Na$_2$SO$_4$) and evaporated under reduced pressure to give a brown oil. The oil was then purified by silica-gel chromatography (10% MeOH/CH$_2$Cl$_2$ as eluant) to give the title compound as a pale yellow oil (0.238 g, 80%), which was crystallised from 60–80 petrol/CH$_2$Cl$_2$.

m.pt 198–200° C. $^1$H NMR (270 MHz, CDCl$_3$), δ 8.61 (dd, 2H), 7.33–6.95 (m, 7H), 6.85 (m, 3H), 3.89 (s, 3H), 3.10 (br s, 4H), 2.62 (br s, 4H), 2.38 (s, 3H), 2.22 (s, 3H).

EXAMPLE 10

N-(4-Methoxy-3-(1-piperazinyl)phenyl)-4-(4-pyridyl)cinnamide

4-Bromocinnamic acid (227 mg, 1.0 mmol) was heated at reflux with thionyl chloride (2 ml) and toluene (40 ml) for 2 h, and then evaporated to dryness under reduced pressure. 1,1-Dimethylethyl 4-(5-amino-2-methyoxyphenyl)-1-piperazinecarboxylate (300 mg, 1.0 mmol) in ThF (10 ml) was added with sodium hydroxide (40 mg) in water (5 ml) and the mixture stirred for 1 h. The solution was partitioned between dichloromethane (40 ml) and water (40 ml), the organic solution dried (sodium sulphate) and evaporated to dryness under reduced pressure to afford an oil, which was purified by column chromatography (silica, EtOAc) to afford the title compound (516 mg, 100%). 1,1-Dimethylethyl 4-[5-(4-bromocinnamoyl)amino]-2-methoxyphenyl-1-piperazinecarboxylate (516 mg, 1.0 mmol), sodium carbonate (106 mg, 1.0 mmol), tetrakis(triphenylphosphine)palladium(0) (49 mg, 0.05 equiv), 4-pyridylboronic acid (123 mg, 1.0 mmol) in water (15 ml) and DME (15 ml) were heated at reflux under argon for 18 h. The solution was partitioned between saturated aqueous potassium carbonate solution (50 ml) and chloroform (50 ml), the organic extracts dried (sodium sulphate), filtered and evaporated to dryness under reduced pressure. The resulting oil was purified by column chromatography (silica, EtOAc) to afford the product as an oil (490 mg, 95%) This product (490 mg, 0.95 mmol) was dissolved in MeOH (50 ml) and conc HCl (5 ml) added. The mixture was heated at reflux for 15 min, cooled, evaporated to dryness, partitioned between saturated aqueous potassium carbonate and chloroform, organic layer dried (sodium sulphate), evaporated to dryness under reduced pressure and purified by flash column chromatography (silica, chloroform/MeOH 5–50%) to afford the title product (210 mg, 53%) which was crystallised from MeOH/ether as the oxalate salt 1H nmr (D6-DMSO) 3.24 (8H, bm, 4×CH$_2$), 3.82 (3H, s), 6.98 (2H, m), 7.40 (2H, m), 7.64 (1H, d), 7.80 (4H, m), 7.92 (2H, d), 8.70 (2H, d), 10.15 (1H, s, NH). Mass Spectrum M$^+$ found 414 C$_{25}$H$_{26}$N$_4$O$_2$ requires 414 Analysis Found C 51.45; H 4.37; N 7.70. C$_{25}$H$_{26}$N$_4$O2–3–9C$_2$H$_2$O$_4$ requires C 51.45; H 4.42; N 7.32.

We claim:

1. A compound of formula (I) or a pharmaceutically acceptable salt thereof:

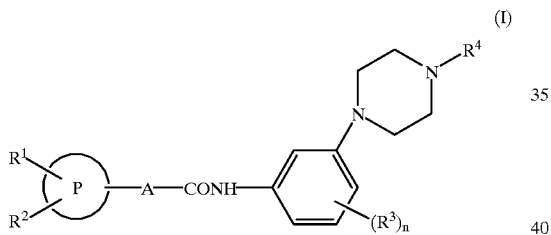

(I)

in which

P is phenyl or thienyl;

R$^1$ is phenyl or pyridyl, both of which are optionally substituted with a substitutent selected from; C$_{1-6}$alkyl, C$_{3-6}$cycloalkyl, C$_{3-6}$cycloalkenyl, C$_{1-6}$alkoxy, hydroxy, cyano, nitro, amino, CO$_2$R$^5$ where R$^5$ is hydrogen or C$_{1-6}$alkyl, or CONR$^5$R$^6$ where R$^6$ and R$^7$ are hydrogen or C$_{1-6}$alkyl;

R$^2$ is hydrogen, halogen, C$_{1-6}$alkyl, C$_{3-6}$cycloalkyl, C$_{3-6}$cycloalkenyl, C$_{1-6}$alkoxy, hydroxy, hydroxyC$_{1-6}$alkyl nitro, trifluoromethyl, cyano, SR$^5$, SOR$^5$, SO$_2$R$^5$, SO$_2$NR$^5$R$^6$, CO$_2$R$^5$ CONR$^5$R$^6$, CONR$^5$(CH$_2$)$_p$ CO$_2$R$^6$, NR$^5$R$^6$, NR$^5$CO$_2$R$^6$, CR$^5$=NOR$^6$, where R$^5$R$^6$, and p are independently hydrogen or C$_{1-6}$alkyl and p is 1 to 3;

R$^3$ is absent or present as halogen, hydroxy, C$_{1-6}$alkyl or C$_{1-6}$alkoxy;

R$^4$ is hydrogen or C$_{1-6}$alkyl;

A is NH; and n is 1 or 2, or a pharmaceutically acceptable salt thereof.

2. A compound according to claim 1 in which R$^2$ is hydrogen or C$_{1-6}$alkyl.

3. A compound according to claim 1 in which R$^3$ is C$_{1-6}$alkoxy.

4. A compound according to claim 1 in which R$^4$ is C$_{1-6}$alkyl.

5. A compound according to claim 1 which is:

N-(4-bromophenyl)-N'-[4-methoxy-3-(4-methyl-1-piperazinyl)phenyl]urea,

N-(4-bromo-3-methylphenyl)-N'-[4-methoxy-3-(4-methyl-1-piperazinyl)phenyl]urea, or N-[3-methyl-4-(4-pyridyl)phenyl]-N'-[4-methoxy-3-(4-methyl-1-piperazinyl)phenyl]urea, and pharmaceutically acceptable salts thereof.

6. A process for the preparation of a compound of formula (I) as claimed in claim 1 which comprises coupling a compound of formula (X):

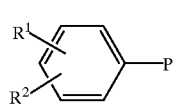

(X)

with a compound of formula (XI):

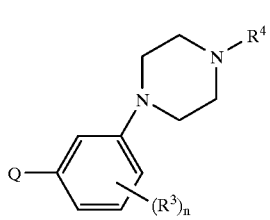

(XI)

wherein R$^1$, R$^2$, R$^3$, R$^4$ and n are as defined in claim 1 and P and Q are functional groups which when coupled form the —NHCONH— linkage;

and then optionally forming a pharmaceutically acceptable salt.

7. A pharmaceutical composition which comprises a compound according to claim 1 in association with a pharmaceutically acceptable carrier or excipient.

8. A method of treating depression or anxiety in a subject which comprises administering an effective amount of a compound of claim 1 or a pharmaceutically acceptable salt thereof.

* * * * *